United States Patent
Manstein et al.

(10) Patent No.: US 9,351,792 B2
(45) Date of Patent: May 31, 2016

(54) METHOD AND APPARATUS FOR DERMATOLOGICAL TREATMENT AND FRACTIONAL SKIN RESURFACING

(75) Inventors: Dieter Manstein, Boston, MA (US); Richard Anderson, Lexington, MA (US)

(73) Assignee: The General Hospital Corporation, Boston, MA (US)

(*) Notice: Subject to any disclaimer, the term of this patent is extended or adjusted under 35 U.S.C. 154(b) by 527 days.

(21) Appl. No.: 11/780,261

(22) Filed: Jul. 19, 2007

(65) Prior Publication Data
US 2008/0021442 A1 Jan. 24, 2008

Related U.S. Application Data

(63) Continuation of application No. 10/542,390, filed as application No. PCT/US2004/009452 on Mar. 25, 2004.

(60) Provisional application No. 60/458,770, filed on Mar. 27, 2003.

(51) Int. Cl.
*A61B 18/20* (2006.01)
*A61B 17/00* (2006.01)
(Continued)

(52) U.S. Cl.
CPC ..... *A61B 18/203* (2013.01); *A61B 2017/00765* (2013.01); *A61B 2018/00023* (2013.01);
(Continued)

(58) Field of Classification Search
CPC .......... A61B 2017/00747–2017/00774; A61B 2018/00452–2018/00476; A61B 2018/00577; A61B 2018/00589–2018/00607; A61B 2018/00625; A61B 2018/00994; A61B 2018/1807; A61B 2018/2005; A61B 2018/2015; A61B 2018/2035; A61B 2018/2065–2018/2095; A61B 18/18; A61B 18/20; A61B 18/201; A61B 18/203; A61B 2019/4036–2019/4054; A61B 2019/409; A61N 5/0616; A61N 5/0644; A61N 5/0645; A61N 5/065; A61N 2005/0658–2005/0662; A61N 2005/067

USPC .................... 606/9–14; 607/88–92
See application file for complete search history.

(56) References Cited

U.S. PATENT DOCUMENTS 3,622,743 A 11/1971 Muncheryan
4,122,853 A 10/1978 Smith
(Continued)

FOREIGN PATENT DOCUMENTS

EP 0172490 2/1986
EP 0880941 12/2001
(Continued)

OTHER PUBLICATIONS

Apfelberg et al; "Dot or Pointillistic Method for Improvement in Results of Hypertrophic Scarring in the Argon Laser Treatment of Portwine Hemangiomas" Lasers in Surg. & Med; vol. 6; 1987; pp. 552-558.*
(Continued)

*Primary Examiner* — Lynsey Crandall
(74) *Attorney, Agent, or Firm* — Andrews Kurth LLP

(57) ABSTRACT

A system and method for performing fractional resurfacing of a target area of skin using electromagnetic radiation are provided. An electromagnetic radiation is generated by an electromagnetic radiation source. The electromagnetic radiation is caused to be applied to a particular portion of a target area of skin. The electromagnetic radiation can be impeded from affecting another portion of the target area of the skin by a mask. Alternatively, the electromagnetic radiation may be applied to portions of the target area of the skin, other than the particular portion.

16 Claims, 5 Drawing Sheets

(51) Int. Cl.
  *A61B 18/00* (2006.01)
  *A61B 19/00* (2006.01)
  *A61N 5/06* (2006.01)

(52) U.S. Cl.
  CPC ............ *A61B2018/0047* (2013.01); *A61B 2018/00452* (2013.01); *A61B 2018/202* (2013.01); *A61B 2018/208* (2013.01); *A61B 2018/2085* (2013.01); *A61B 2019/409* (2013.01); *A61B 2019/4036* (2013.01); *A61B 2019/4054* (2013.01); *A61N 2005/0665* (2013.01)

(56) References Cited

U.S. PATENT DOCUMENTS

| | | | |
|---|---|---|---|
| 4,396,285 | A | 8/1983 | Presta et al. |
| 4,556,057 | A | 12/1985 | Hiruma et al. |
| 4,573,465 | A | 3/1986 | Sugiyama et al. |
| 4,587,396 | A | 5/1986 | Rubin |
| 4,641,650 | A | 2/1987 | Mok |
| 4,653,495 | A | 3/1987 | Nanaumi |
| 4,669,466 | A | 6/1987 | L'Esperance |
| 4,672,969 | A | 6/1987 | Dew |
| 4,718,416 | A | 1/1988 | Nanaumi |
| 4,733,660 | A | 3/1988 | Itzkan |
| 4,775,361 | A | 10/1988 | Jacques et al. |
| 4,784,135 | A | 11/1988 | Blum et al. |
| 4,917,083 | A | 4/1990 | Harrington et al. |
| 4,930,504 | A | 6/1990 | Diamantopoulos et al. |
| 4,976,709 | A | 12/1990 | Sand |
| 5,000,752 | A | 3/1991 | Hoskin et al. |
| 5,002,051 | A | 3/1991 | Dew et al. |
| 5,076,669 | A | 12/1991 | Black et al. |
| 5,104,392 | A | 4/1992 | Kittrell |
| 5,106,387 | A | 4/1992 | Kittrell et al. |
| 5,114,218 | A | 5/1992 | Black et al. |
| 5,128,509 | A | 7/1992 | Black et al. |
| 5,139,494 | A | 8/1992 | Freiberg |
| 5,144,630 | A | 9/1992 | Lin |
| 5,151,600 | A | 9/1992 | Black |
| 5,163,935 | A | 11/1992 | Black et al. |
| 5,163,936 | A | 11/1992 | Black et al. |
| 5,178,617 | A | 1/1993 | Kuizenga et al. |
| 5,184,156 | A | 2/1993 | Black et al. |
| 5,192,278 | A | 3/1993 | Hayes et al. |
| 5,282,797 | A | 2/1994 | Chess |
| 5,302,259 | A | 4/1994 | Bimgruber |
| 5,312,395 | A | 5/1994 | Tan et al. |
| 5,312,396 | A | 5/1994 | Feld et al. |
| 5,318,024 | A | 6/1994 | Kittrell et al. |
| 5,336,217 | A | 8/1994 | Buys et al. |
| 5,339,347 | A | 8/1994 | Slatkin et al. |
| 5,360,447 | A | 11/1994 | Koop |
| 5,382,770 | A | 1/1995 | Black et al. |
| 5,382,986 | A | 1/1995 | Black et al. |
| 5,411,502 | A | 5/1995 | Zair |
| 5,420,882 | A | 5/1995 | Black |
| 5,421,337 | A | 6/1995 | Richards-Kortum et al. |
| 5,423,803 | A | 6/1995 | Tankovich et al. |
| 5,449,882 | A | 9/1995 | Black et al. |
| 5,474,549 | A | 12/1995 | Ortiz et al. |
| 5,531,740 | A | 7/1996 | Black |
| 5,546,214 | A | 8/1996 | Black et al. |
| 5,558,666 | A | 9/1996 | Dewey et al. |
| 5,582,752 | A | 12/1996 | Zair |
| 5,586,981 | A | 12/1996 | Hu |
| 5,595,568 | A | 1/1997 | Anderson et al. |
| 5,611,795 | A | 3/1997 | Slatkine et al. |
| 5,616,140 | A | 4/1997 | Prescott |
| 5,618,284 | A | 4/1997 | Sand |
| 5,618,285 | A | 4/1997 | Zair |
| 5,624,434 | A | 4/1997 | Abergel et al. |
| 5,628,744 | A | 5/1997 | Coleman et al. |
| 5,632,741 | A | 5/1997 | Zavislan et al. |
| 5,643,252 | A | 7/1997 | Waner et al. |
| 5,655,547 | A | 8/1997 | Karni |
| 5,693,043 | A | 12/1997 | Kittrell |
| 5,713,364 | A | 2/1998 | DeBaryshe et al. |
| 5,733,278 | A | 3/1998 | Slatkine et al. |
| 5,735,843 | A | 4/1998 | Trokel |
| 5,735,844 | A | 4/1998 | Anderson et al. |
| 5,746,735 | A | 5/1998 | Furumoto et al. |
| 5,759,200 | A | 6/1998 | Azar |
| 5,786,924 | A | 7/1998 | Black et al. |
| 5,798,498 | A | 8/1998 | Zair |
| 5,807,386 | A | 9/1998 | Slatkine et al. |
| 5,810,801 | A | 9/1998 | Anderson et al. |
| 5,814,042 | A | 9/1998 | Zair |
| 5,817,089 | A | 10/1998 | Tankovich et al. |
| 5,830,208 | A | 11/1998 | Muller |
| 5,843,073 | A | 12/1998 | Sinofsky |
| 5,860,967 | A | 1/1999 | Zavislan et al. |
| 5,860,968 | A | 1/1999 | Wojcik et al. |
| 5,865,754 | A | 2/1999 | Sevick-Muraca et al. |
| 5,873,875 | A | 2/1999 | Altshuler |
| 5,879,326 | A | 3/1999 | Godshall et al. |
| 5,885,211 | A * | 3/1999 | Eppstein et al. ............... 600/309 |
| 5,897,549 | A | 4/1999 | Tankovich |
| 5,906,609 | A | 5/1999 | Assa et al. |
| 5,908,415 | A | 6/1999 | Sinofsky |
| 5,925,035 | A | 7/1999 | Tankovich |
| 5,938,657 | A | 8/1999 | Assa et al. |
| 5,947,956 | A | 9/1999 | Karell |
| 5,951,543 | A | 9/1999 | Brauer |
| 5,957,915 | A | 9/1999 | Trost |
| 5,964,749 | A | 10/1999 | Eckhouse et al. |
| 5,968,033 | A | 10/1999 | Fuller et al. |
| 5,970,983 | A | 10/1999 | Karni et al. |
| 5,983,900 | A | 11/1999 | Clement et al. |
| 5,984,915 | A | 11/1999 | Loeb et al. |
| 5,995,265 | A | 11/1999 | Black et al. |
| 5,995,866 | A | 11/1999 | Lemelson |
| 6,011,809 | A | 1/2000 | Tosaka |
| 6,015,404 | A | 1/2000 | Altshuler et al. |
| 6,022,316 | A | 2/2000 | Eppstein et al. |
| 6,027,496 | A | 2/2000 | Loomis et al. |
| RE36,634 | E | 3/2000 | Ghaffari |
| 6,036,684 | A | 3/2000 | Tankovich et al. |
| 6,050,990 | A | 4/2000 | Tankovich et al. |
| 6,059,820 | A | 5/2000 | Baronov |
| 6,063,108 | A | 5/2000 | Salansky et al. |
| 6,074,384 | A | 6/2000 | Brinkmann et al. |
| 6,083,217 | A | 7/2000 | Tankovich |
| 6,096,029 | A | 8/2000 | O'Donnell, Jr. |
| 6,096,031 | A | 8/2000 | Mitchell et al. |
| 6,104,959 | A | 8/2000 | Spertell |
| 6,106,514 | A | 8/2000 | O'Donnell, Jr. |
| RE36,872 | E | 9/2000 | Zair |
| 6,113,559 | A | 9/2000 | Klopotek |
| 6,120,497 | A | 9/2000 | Anderson et al. |
| 6,142,939 | A | 10/2000 | Eppstein |
| 6,142,939 | A | 11/2000 | Eppstein |
| 6,149,644 | A | 11/2000 | Xie |
| 6,149,645 | A | 11/2000 | Tobinick |
| 6,152,917 | A | 11/2000 | Tankovich |
| 6,162,211 | A | 12/2000 | Tankovich et al. |
| 6,162,213 | A | 12/2000 | Stewart |
| 6,165,170 | A | 12/2000 | Wynne et al. |
| 6,168,590 | B1 | 1/2001 | Neev |
| 6,171,302 | B1 | 1/2001 | Talpalriu et al. |
| 6,173,202 | B1 | 1/2001 | Eppstein |
| 6,176,854 | B1 | 1/2001 | Cone |
| 6,183,773 | B1 | 2/2001 | Anderson |
| 6,197,020 | B1 | 3/2001 | O'Donnell, Jr. |
| 6,201,608 | B1 | 3/2001 | Mandella et al. |
| 6,201,639 | B1 | 3/2001 | Overbeck |
| 6,207,958 | B1 | 3/2001 | Giakos |
| 6,208,411 | B1 | 3/2001 | Vaez-Iravani |
| 6,208,673 | B1 | 3/2001 | Miyake |
| 6,208,886 | B1 | 3/2001 | Alfano et al. |
| 6,211,484 | B1 | 4/2001 | Kaplan et al. |
| 6,211,988 | B1 | 4/2001 | Engelhardt et al. |
| 6,214,560 | B1 | 4/2001 | Yguerabide et al. |

(56) References Cited

U.S. PATENT DOCUMENTS

| | | | |
|---|---|---|---|
| 6,215,586 B1 | 4/2001 | Clark | |
| 6,219,142 B1 | 4/2001 | Kane | |
| 6,219,461 B1 | 4/2001 | Wallack | |
| 6,219,575 B1 | 4/2001 | Nemati | |
| 6,222,664 B1 | 4/2001 | Dorsel | |
| 6,225,636 B1 | 5/2001 | Ginestet | |
| 6,229,138 B1 | 5/2001 | Kley | |
| 6,232,092 B1 | 5/2001 | Rogers | |
| 6,232,597 B1 | 5/2001 | Kley | |
| 6,233,055 B1 | 5/2001 | Mandella et al. | |
| 6,234,633 B1 | 5/2001 | Birngruber et al. | |
| 6,235,015 B1 | 5/2001 | Mead, III et al. | |
| 6,239,909 B1 | 5/2001 | Hayashi et al. | |
| 6,241,753 B1 | 6/2001 | Knowlton | |
| 6,242,734 B1 | 6/2001 | Kley | |
| 6,243,189 B1 | 6/2001 | Ribes et al. | |
| 6,245,060 B1 | 6/2001 | Loomis et al. | |
| 6,248,103 B1 | 6/2001 | Tannenbaum et al. | |
| 6,248,988 B1 | 6/2001 | Krantz | |
| 6,249,347 B1 | 6/2001 | Svetkoff et al. | |
| 6,249,630 B1 | 6/2001 | Stock et al. | |
| 6,251,099 B1 | 6/2001 | Kollias et al. | |
| 6,251,100 B1 | 6/2001 | Flock et al. | |
| 6,252,666 B1 | 6/2001 | Mandella et al. | |
| 6,255,642 B1 | 7/2001 | Cragg et al. | |
| 6,259,104 B1 | 7/2001 | Baer | |
| 6,266,148 B1 | 7/2001 | Engelhardt et al. | |
| 6,267,771 B1 | 7/2001 | Tankovich et al. | |
| 6,269,197 B1 | 7/2001 | Wallack | |
| 6,273,884 B1 | 8/2001 | Altshuler et al. | |
| 6,273,885 B1 | 8/2001 | Koop et al. | |
| 6,277,116 B1 | 8/2001 | Utely et al. | |
| 6,280,960 B1 | 8/2001 | Carr | |
| 6,281,491 B1 | 8/2001 | Kley | |
| 6,282,011 B1 | 8/2001 | Tearney et al. | |
| 6,285,002 B1 | 9/2001 | Ngoi et al. | |
| 6,285,019 B1 | 9/2001 | Engelhardt et al. | |
| 6,300,639 B1 | 10/2001 | Wiederhoeft | |
| 6,304,316 B1 | 10/2001 | Jain et al. | |
| 6,304,373 B1 | 10/2001 | Zavislan | |
| 6,315,772 B1 | 11/2001 | Marchitto et al. | |
| 6,325,769 B1 | 12/2001 | Klopotek | |
| 6,328,733 B1 | 12/2001 | Trost | |
| 6,350,261 B1 | 2/2002 | Domankevitz et al. | |
| 6,375,672 B1 | 4/2002 | Aksan et al. | |
| 6,387,089 B1 | 5/2002 | Kreindel et al. | |
| 6,391,022 B1 | 5/2002 | Furumoto et al. | |
| 6,395,000 B1 | 5/2002 | Mitchell et al. | |
| 6,406,474 B1 | 6/2002 | Neuberger et al. | |
| 6,413,267 B1 | 7/2002 | Dumoulin-White et al. | |
| 6,428,532 B1 | 8/2002 | Doukas et al. | |
| 6,436,127 B1 | 8/2002 | Anderson et al. | |
| 6,440,155 B1 | 8/2002 | Matsumae et al. | |
| 6,443,946 B2 | 9/2002 | Clement et al. | |
| 6,443,978 B1 | 9/2002 | Zharov | |
| 6,445,491 B2 | 9/2002 | Sucha et al. | |
| 6,468,229 B1 | 10/2002 | Grace et al. | |
| 6,475,138 B1 | 11/2002 | Schechter et al. | |
| 6,508,813 B1 | 1/2003 | Altshuler | |
| 6,511,475 B1 | 1/2003 | Altshuler et al. | |
| 6,514,244 B2 | 2/2003 | Pope et al. | |
| 6,514,278 B1 | 2/2003 | Hibst et al. | |
| 6,517,532 B1 * | 2/2003 | Altshuler et al. | 606/9 |
| 6,529,543 B1 | 3/2003 | Anderson et al. | |
| 6,530,915 B1 | 3/2003 | Eppstein et al. | |
| 6,533,776 B2 | 3/2003 | Asah et al. | |
| 6,537,270 B1 | 3/2003 | Elbrecht et al. | |
| 5,569,156 A1 | 5/2003 | Tankovich et al. | |
| 6,562,004 B1 | 5/2003 | Doukas et al. | |
| 6,569,155 B1 | 5/2003 | Connors et al. | |
| 6,569,156 B1 | 5/2003 | Tankovich et al. | |
| 6,572,637 B1 | 6/2003 | Yamazaki et al. | |
| 6,575,963 B1 | 6/2003 | Van Saarloos et al. | |
| 6,579,283 B1 | 6/2003 | Tobinick | |
| 6,585,725 B1 | 7/2003 | Mukai | |
| 6,605,080 B1 | 8/2003 | Altshuler et al. | |
| 6,607,523 B1 | 8/2003 | Asah et al. | |
| 6,613,040 B2 | 9/2003 | Tankovich et al. | |
| 6,613,042 B1 | 9/2003 | Tankovich et al. | |
| 6,632,219 B1 | 10/2003 | Baranov et al. | |
| 6,652,512 B2 | 11/2003 | Ota | |
| 6,653,618 B2 | 11/2003 | Zenzie | |
| 6,659,999 B1 | 12/2003 | Anderson et al. | |
| 6,673,095 B2 | 1/2004 | Nordquist | |
| 6,676,654 B1 | 1/2004 | Balle-Petersen et al. | |
| 6,680,999 B1 | 1/2004 | Garcia | |
| 6,685,699 B1 | 2/2004 | Eppstein et al. | |
| 6,695,835 B2 | 2/2004 | Furuno et al. | |
| 6,706,032 B2 | 3/2004 | Weaver et al. | |
| 6,717,102 B2 | 4/2004 | Neev et al. | |
| 6,723,090 B2 | 4/2004 | Altshuler et al. | |
| 6,743,211 B1 | 6/2004 | Prausnitz et al. | |
| 6,758,845 B1 | 7/2004 | Weckwerth et al. | |
| 6,766,202 B2 | 7/2004 | Underwood et al. | |
| 6,824,540 B1 | 11/2004 | Lin | |
| 6,836,278 B2 | 12/2004 | Saito et al. | |
| 6,855,117 B2 * | 2/2005 | Skover | 600/584 |
| 6,881,212 B1 | 4/2005 | Clement et al. | |
| 6,997,923 B2 * | 2/2006 | Anderson et al. | 606/9 |
| 7,006,874 B2 | 2/2006 | Knowlton et al. | |
| 7,135,033 B2 | 11/2006 | Altshuler et al. | |
| 7,204,832 B2 | 4/2007 | Altshuler et al. | |
| 2001/0007068 A1 | 7/2001 | Ota et al. | |
| 2001/0023351 A1 | 9/2001 | Eilers et al. | |
| 2002/0002367 A1 | 1/2002 | Tankovich et al. | |
| 2002/0052547 A1 | 5/2002 | Toida | |
| 2002/0062142 A1 | 5/2002 | Knowlton | |
| 2002/0091377 A1 | 7/2002 | Anderson et al. | |
| 2002/0138072 A1 | 9/2002 | Black et al. | |
| 2002/0161357 A1 | 10/2002 | Anderson et al. | |
| 2002/0173780 A1 | 11/2002 | Altshuler et al. | |
| 2003/0032950 A1 | 2/2003 | Altshuler et al. | |
| 2003/0034959 A1 | 2/2003 | Davis et al. | |
| 2003/0055413 A1 | 3/2003 | Altshuler et al. | |
| 2003/0109787 A1 | 6/2003 | Black | |
| 2003/0109860 A1 | 6/2003 | Black | |
| 2003/0216719 A1 * | 11/2003 | Debenedictis et al. | 606/10 |
| 2004/0015157 A1 | 1/2004 | Connors et al. | |
| 2004/0093042 A1 | 5/2004 | Altshuler et al. | |
| 2004/0143247 A1 | 7/2004 | Anderson et al. | |
| 2004/0152943 A1 | 8/2004 | Zimmerman et al. | |
| 2005/0015077 A1 | 1/2005 | Kuklin et al. | |
| 2005/0049582 A1 | 3/2005 | DeBenedictis et al. | |
| 2005/0154382 A1 | 7/2005 | Altshuler et al. | |
| 2005/0203491 A1 | 9/2005 | Khomchenko | |
| 2005/0222565 A1 | 10/2005 | Manstein | |
| 2005/0283141 A1 | 12/2005 | Giovannoli | |
| 2006/0009750 A1 | 1/2006 | Altshuler et al. | |
| 2006/0282135 A1 | 12/2006 | Tankovich | |

FOREIGN PATENT DOCUMENTS

| | | | |
|---|---|---|---|
| WO | 99/27997 | 6/1999 | |
| WO | 00/53261 | 9/2000 | |
| WO | 00/67917 | 11/2000 | |
| WO | 00/71045 | 11/2000 | |
| WO | 00/78242 | 12/2000 | |
| WO | 01/26573 | 4/2001 | |
| WO | 01/39834 | 6/2001 | |
| WO | 01/74265 | 10/2001 | |
| WO | WO 02/053050 | * 7/2002 | 607/89 |
| WO | 02/089688 | 11/2002 | |

OTHER PUBLICATIONS

Unger "Hair Transplantation III Computer Assisted Laser Transplanting"; Dermatol Surg; vol. 21; 1995; pp. 1047-1055.*
Dieter Manstein et al. "Fractional Photothermolysis: A New Concept for Cutaneous Remodeling Using Microscopic Patterns of Thermal Injury" Lasers in Surgery and Medicine 9999:1-13 (2004).
European Search Report dated Dec. 14, 2010 for EP 10182989.3.
European Search Report dated Dec. 22, 2010 for EP 10183016.4.
Anderson et al: U.S. Appl. No. 60/258,855, filed Dec. 28, 200; pp. 1-3, 5, 6, 8-15 ands Figures 22A and 22B.

(56) References Cited

OTHER PUBLICATIONS

Fitzpatrick, R.E. "Laser hair Transplantation. Tissue effects of Laser Parameters," Dermatol. Surg., Dec. 1995, pp. 1042-1046, vol. 21. No. 12.

Grevelink, J.M., "Laser Hair Transplantation,"Dermatologic Clinics, Jul. 1, 1997, pp. 479-486, vol. 15, Issue 3.

Mckenzie, A.L., "a Three-Zone Model of Tissue Damage by a C02 Laser," Phys. Med Boil, 1986, pp. 967-983, vol. 31, No. 9.

Rubach, B.W. et al., "Histological and Clinical Evolution of Facial Resurfacing Using a Carbon Dioxide Laser with the Computer Pattern Generator," Arch. Otolaryngol. Head Neck Surg., Sep. 1997, pp. 929-934, vol. 123, No. 9.

Unger, W.P. et al., "Laser Hair Transplantation," J. Dermatol. Surg. Oncol., Aug. 1994, pp. 515-521. vol. 20, No. 8.

Australian Examination Report, AU 2003284336, Feb. 12, 2008, 3 pages.

PCT International Search Report and Written Opinion, PCT/US07/03694, Feb. 22, 2008, 12 pages.

Fuji, H. et al., "Multispot Laser Photocoagulation System Using a Fiber Bundle Scanner," Applied Optics, Oct. 1, 1982, pp. 3437-3442.

Mordon, S, et al., "Using a "Non Uniform Pulse Sequence" can Improve Selective Coagulation with a Nd: YAG Laser (1.06um) Thanks to Met-Hemoglobin Absorption: A Clinical Study on Blue Log Veins," Lasers in Surgery and Medicine, 2003, pp. 160-170, vol. 32.

Naess, E. et al., "Computer-Assisted Laser Photocoagulation of the Retina—a ybrid Tracking Approach," Journal of Biomedical Optics, Apr. 2002, pp. 179-189. vol. 7, No. 2.

Partovi, F. et al., "A Model for Thermal Ablation of Biological Tissue Using Laser Radiation," Lasers in Surgery and Medicine, 1987, pp. 141-154, vol. 7.

US 6,344,051, 2/2002, Dumoulin-Wite et al. (withdrawn).

Anderson, Dan E. et al. "System for the Automated Photothermal Treatment of Cutaneous Vascular Lesions" Journal of Biomedical Optics 9(2), 308-314 (Mar./Apr. 2004).

Fujii H. et al. "Fiber bundle scanner for laser photocoagulation" Optics and Laser Technology, p. 39-40, (Feb. 1982).

Notification of International Search Report or the Declaration, PCT/US03/33597, Jul. 25, 2005, 4 pages.

Anderson, R.R. and E.V. Ross, "Laser-Tissue Interactions", "Cosmetic Laser Surgery", 2000, pp. 1-30, Mosby.

European Office Action for European Patent Application No. 10 183 016.4 dated May 15, 2012.

European Office Action for European Patent Application No. 10 183 064.4 dated Jul. 20, 2012.

European Office Action for European Patent Application No. 10 182 989.3 dated Jul. 20, 2012.

Apfelberg et al.; (1995) "Intralesional Laser Photocoagulation-Steroids as an Adjunct to Surgery for Massive Hemangiomas and Vascular Malformations" Ann Plast Surg: 35:144-149.

Unger et al. (1994) "Laser Hair Transplantation" Elsevier Science Inc. vol. 94, pp. 148-812.

* cited by examiner

A - A

METHOD AND APPARATUS FOR DERMATOLOGICAL TREATMENT AND FRACTIONAL SKIN RESURFACING

CROSS REFERENCE TO RELATED APPLICATIONS

The present application claims priority from U.S. Provisional Patent Application Ser. No. 60/458,770 filed Mar. 27, 2003. The present application is also a continuation of U.S. patent application Ser. No. 10/542,390 filed Jul. 13, 2005, which is a U.S. National Phase of International Application No. PCT/US04/09452 filed Mar. 25, 2004. The entire disclosures of the applications referenced above are incorporated herein by reference.

BACKGROUND OF THE INVENTION

1. Field of the Invention

The present invention relates to methods and apparatus that use electromagnetic radiation for dermatological treatment and, more particularly to a method and apparatus that use optical radiation to ablate or damage a target area of skin surface for dermatological treatment, which skin surface includes the epidermis and parts of the dermis as the objective or side effect of the desired treatment.

2. Background Art

There is an increasing demand for repair of or improvement to skin defects, which can be induced by aging, sun exposure, dermatological diseases, traumatic effects, and the like. Many treatments which use electromagnetic radiation have been used to improve skin defects by inducing a thermal injury to the skin, which results in a complex wound healing response of the skin. This leads to a biological repair of the injured skin.

Various techniques providing this objective have been introduced in recent years. The different techniques can be generally categorized in two groups of treatment modalities: ablative laser skin resurfacing ("LSR") and non-ablative collagen remodeling ("NCR"). The first group of treatment modalities, i.e., LSR, includes causing thermal damage to the epidermis and/or dermis, while the second group, i.e., NCR, is designed to spare thermal damage of the epidermis.

LSR with pulsed $CO_2$ or Er:YAG lasers, which may be referred to in the art as laser resurfacing or ablative resurfacing, is considered to be an effective treatment option for signs of photo aged skin, chronically aged skin, scars, superficial pigmented lesions, stretch marks, and superficial skin lesions. However, patients may experience major drawbacks after each LSR treatment, including edema, oozing, and burning discomfort during first fourteen (14) days after treatment. These major drawbacks can be unacceptable for many patients. A further problem with LSR procedures is that the procedures are relatively painful and therefore generally require an application of a significant amount of analgesia. While LSR of relatively small areas can be performed under local anesthesia provided by injection of an anestheticum, LSR of relatively large areas is frequently performed under general anesthesia or after nerve blockade by multiple injections of anesthetic.

Any LSR treatment results in thermal skin damage to the treatment area of the skin surface, including the epidermis and/or the dermis. LSR treatment with pulsed $CO_2$ lasers is particularly aggressive, causing thermal skin damage to the epidermis and at least to the superficial dermis. Following LSR treatment using $CO_2$ lasers, a high incidence of complications can occur, including persistent erythema, hyperpigmentation, hypopigmentation, scarring, and infection (e.g., infection with Herpes simplex virus). LSR treatment with the Er:YAG laser has been introduced as a more gentle alternative to the $CO_2$ laser, due to the lesser penetration depth of the Er:YAG pulsed laser. Using the Er:YAG laser results in a thinner zone of thermal injury within the residual tissue of the target area of the skin. However, LSR that uses the Er:YAG laser produces side effects similar to those made by LSR that uses the $CO_2$ laser within the first days after treatment.

A limitation of LSR using $CO_2$ or Er:YAG lasers is that ablative laser resurfacing generally can not be performed on the patients with dark complexions. The removal of pigmented epidermis tissue can cause severe cosmetic disfigurement to patients with a dark complexion, which may last from several weeks up to years, which is considered by most patients and physicians to be unacceptable. Another limitation of LSR is that ablative resurfacing in areas other than the face generally have a greater risk of scarring. LSR procedures in areas other than the face result in an increased incidence of an unacceptable scar formation because the recovery from skin injury within these areas is not very effective.

In an attempt to overcome the problems associated with LSR procedures, a group of NCR techniques has emerged. These techniques are variously referred to in the art as non-ablative resurfacing, non-ablative subsurfacing, or non-ablative skin remodeling. NCR techniques generally utilize non-ablative lasers, flashlamps, or radio frequency current to damage dermal tissue while sparing damage to the epidermal tissue. The concept behind NCR techniques is that the thermal damage of only the dermal tissues is thought to induce wound healing which results in a biological repair and a formation of new dermal collagen. This type of wound healing can result in a decrease of photoaging related structural damage. Avoiding epidermal damage in NCR techniques decreases the severity and duration of treatment related side effects. In particular, post procedural oozing, crusting, pigmentary changes and incidence of infections due to prolonged loss of the epidermal barrier function can usually be avoided by using the NCR techniques.

Various strategies are presently applied using nonablative lasers to achieve damage to the dermis while sparing the epidermis. Nonablative lasers used in NCR procedures have a deeper dermal penetration depth as compared to ablative lasers used in LSR procedures. Wavelengths in the near infrared spectrum can be used. These wavelengths cause the non-ablative laser to have a deeper penetration depth than the very superficially-absorbed ablative Er:YAG and $CO_2$ lasers. The dermal damage is achieved by a combination of proper wavelength and superficial skin cooling, or by focusing a laser into the dermis with a high numerical aperture optic in combination with superficial skin cooling. While it has been demonstrated that these techniques can assist in avoiding epidermal damage, one of the major drawbacks of these techniques is their limited efficacies. The improvement of photoaged skin or scars after the treatment with NCR techniques is significantly smaller than the improvements found when LSR ablative techniques are utilized. Even after multiple treatments, the clinical improvement is often far below the patient's expectations. In addition, clinical improvement is usually several months delayed after a series of treatment procedures.

Another limitation of NCR procedures relates to the breadth of acceptable treatment parameters for safe and effective treatment of dermatological disorders. The NCR procedures generally rely on an optimum coordination of laser energy and cooling parameters, which can result in an unwanted temperature profile within the skin leading to either no therapeutic effect or scar formation due to the overheating of a relatively large volume of the tissue.

Yet another problem of non-ablative procedures relates to the sparing of the epidermis. While sparing the epidermis is advantageous in order to decrease the side effects related to complete removal of the epidermis, several applications of NCR procedures may benefit from at least partial removal of epidermal structures. For example, photoinduced skin aging manifests not only by the dermal alterations, but also by epidermal alterations.

A further problem of both ablative and nonablative resurfacing is that the role of keratinocytes in the wound healing response is not capitalized upon. Keratinocyte plays an active role in the wound healing response by releasing cytokines when the keratinocyte is damaged. During traditional ablative resurfacing procedures, the keratinocytes are removed from the skin along with the epidermis, thereby removing them from the healing process altogether. On the other hand, in traditional non-ablative procedures, the keratinocytes, which are located in the epidermis, are not damaged, therefore they do not release cytokines to aid in the healing process.

Another major problem with all LSR and NCR techniques now used is the appearance of visible spots and/or edges after treatment due to inflammation, pigmentation, or texture changes, corresponding to the sites of treatment. Devices for LSR and NCR produce macroscopic (easily seen) sexposure areas. For example, laser exposure spot diameters typically vary from about 1 to 10 mm, and NCR exposure spot diameters from about 3 to 50 mm. Some devices, such as indense pulsed light devices, leave "boxes" of skin response due to rectangular output patterns on the skin. Patients do not like such spot or box patterns, easily seen as red, brown or white areas ranging from on the order of millimeters to centimeters in size, which remain for days or even years after treatment.

Therefore, there is a need to provide a procedure and apparatus that combine safe and effective treatment for improvement of dermatological disorders with minimum side effects, such as intra procedural discomfort, post procedural discomfort, lengthy healing time, and post procedural infection.

SUMMARY OF THE INVENTION

It is therefore one of the objects of the present invention to provide an apparatus and method that combines safe and effective treatment for an improvement of dermatological disorders with minimum side effects. Another object of the present invention is to provide an apparatus and method that cause thermal skin damage to only a fraction of a target area of skin.

These and other objects can be achieved with the exemplary embodiment of the apparatus and method according to the present invention, in which portions of a target area to be subjected to irradiation are masked. The exemplary apparatus can include at least one shielding member configured to mask at least one portion of a target area of skin from electromagnetic radiation, in which the shielding members are formed such that a minimal amount of electromagnetic radiation is reflected back towards an electromagnetic radiation source.

In another advantageous embodiment of the present invention, electromagnetic radiation can be generated by an electromagnetic radiation source, thus causing the electromagnetic radiation to be applied to a target area of the skin. At least one portion of the target area of the skin is then masked from the electromagnetic radiation using a mask.

In yet another advantageous embodiment of the present invention, an apparatus and method for treating dermatological conditions is provided. In particular, a delivery module and translator are utilized. The delivery module is configured to direct electromagnetic radiation generated by an electromagnetic radiation source to a predetermined area within a target area of skin, wherein the predetermined area is located in a location relative to the delivery module, and wherein the electromagnetic radiation is adapted to cause thermal damage to epidermal tissue and dermal tissue of the predetermined area within the target area of the skin. The translator is capable of moving the delivery module, such that the delivery module targets a plurality of spatially separated individual exposure areas of the predetermined area.

In a further advantageous embodiment of the present invention, the electromagnetic radiation can be applied to a first individual exposure area of the target area of the skin. The electromagnetic radiation can then be applied to a second individual exposure area of the target area of the skin, which is separated from the first individual exposure area by a non-irradiated skin section.

BRIEF DESCRIPTION OF THE DRAWINGS

For a more complete understanding of the present invention and its advantages, reference is now made to the following description, taken in conjunction with the accompanying drawings, in which.

Figure 1A:
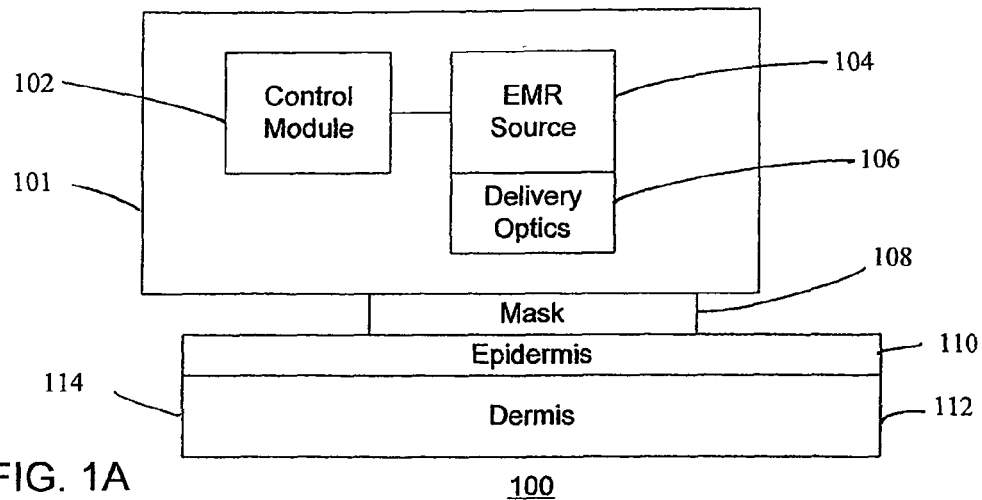
FIGS. 1A-1C show progressive illustrations of a first exemplary embodiment of a fractional resurfacing system for conducting various dermatological treatments at various stages of use according to the present invention.

Throughout the drawings, the same reference numerals and characters, unless otherwise stated, are used to denote like features, elements, components, or portions of the illustrated embodiments. Moreover, while the present invention will now be described in detail with reference to the Figures, it is done so in connection with the illustrative embodiments.

DETAILED DESCRIPTION OF THE PREFERRED EMBODIMENTS

FIGS. 1A-9 illustrate various embodiments of a method and apparatus for fractional resurfacing of a target area of skin. Generally, the exemplary methods and apparatus deliver an electromagnetic radiation to the patient's skin defined by various patterns, so as to induce thermal injury of the skin surface corresponding to such patterns and involving only a fraction of the targeted surface area of the skin. Such technique combines the efficacy of ablative resurfacing procedures with the minimal side effects of non-ablative procedures. The delivery of the electromagnetic radiation to the skin in a predetermined pattern is achieved by either masking parts of the target area of the skin surface in order to protect the masked parts of the skin surface from the electromagnetic radiation, or by utilizing a light beam of relatively small diameter which is scanned across the skin surface by various means in order to generate a specific pattern for affecting superficial thermal skin injury.

Fractional resurfacing is defined as the controlled ablation, removal, destruction, damage or stimulation of multiple small (generally less than 1 mm) individual exposure areas of skin tissue with intervening spared areas of skin tissue, performed as a treatment to improve the skin. The individual exposure areas may be oval, circular, arced and/or linear in shape. The spatial scale of fractional resurfacing is chosen to avoid the appearance of various spots or boxes on a macroscopic scale, while still providing effective treatment because the multiple small areas can be exposed to greater than a minimal stimulus. For example, removal or photothermal destruction of thousands of 0.1 mm diameter individual exposure areas, spaced 0.2 mm apart, and extending into the skin up to a depth of 0.5 mm, is well tolerated and produces effective improvement of photoaging, without apparent spots and with rapid healing. Spared skin between the individual exposure areas rapidly initiates a wound healing response, which is better tolerated than conventional LSR.

During the exemplary fractional resurfacing procedure of the present invention, certain portions of the target area remain undamaged, thereby preserving keratinocytes and melanocytes, which serve as a pool of undamaged cells to promote reepithelialization. This procedure differs from the traditional resurfacing procedures, such that the entirety of the target area is damaged. In traditional resurfacing procedures, reepithelialization is generally initiated from the depth of an undamaged follicular epithelium. Because the traditional procedures remove the entire epithelium, an important factor for the time of reepithelization is the density of follicles. The vellus hair density of the face (439 hairs/cm$^2$) of the subject is significantly higher than on the back of the subject (85 hairs/cm$^2$). Therefore, the face of the subject, generally experiences better and faster reepithelization in comparison to other body areas with a lower hair density.

The resurfacing of the dark pigmented skin is currently not very frequently performed because of the prolonged repigmentation process. The fractional resurfacing technique improves the repigmentation process but, melanocytes do not migrate well. By sparing certain portions of the target area of the skin, the travel distance of melanocytes can be decreased, thereby reducing the repigmentation time and allowing the resurfacing of all skin types.

Figure 1B:
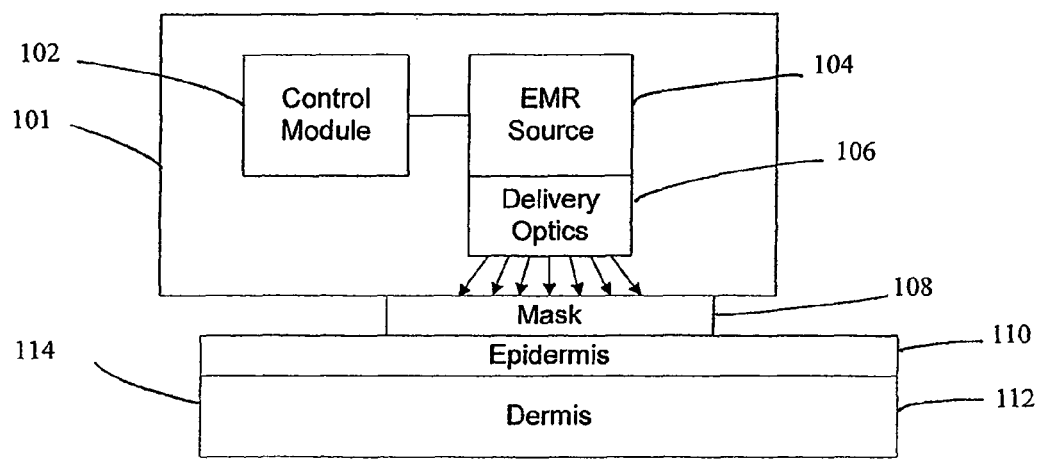
Figure 1C:
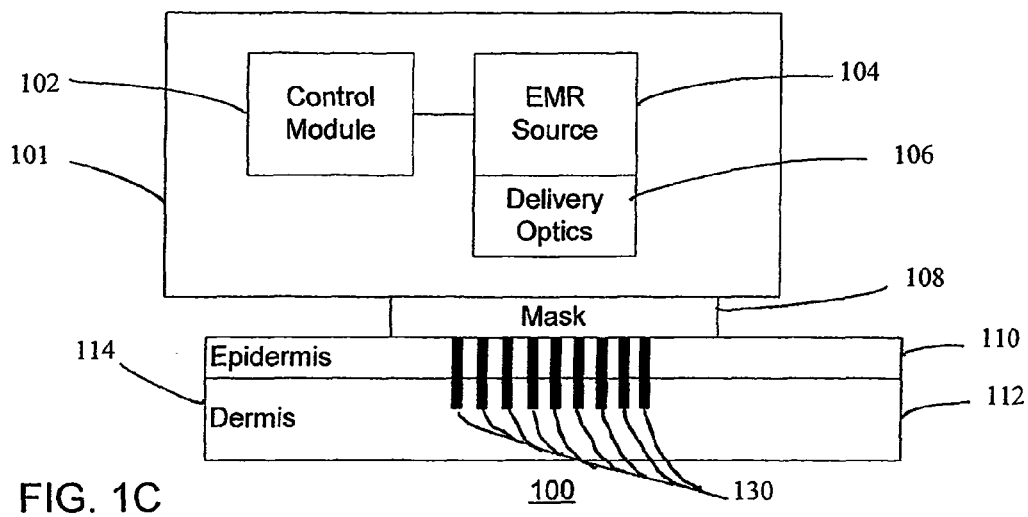

FIGS. 1A-1C illustrate a progressive use of a first exemplary embodiment of a fractional resurfacing system 100 for conducting various dermatological treatments using electromagnetic radiation ("EMR") and generating a superficial pattern of skin damage of a target area by using a mask according to the present invention. The system 100 may be used for collagen remodeling, removal of unwanted pigment or tattoo, and/or other dermatological applications. As shown in FIGS. 1A-1C, the system 100 includes a case 101, a control module 102, an EMR source 104, delivery optics 106 and a mask 108. The case 101 contains the control module 102, the EMR source 104, and the delivery optics 106. An aperture is provided through a sidewall of the case 101. The mask 108 is placed in registration with the aperture formed through the sidewall of the case 101. By placing the mask 108 in registration with the aperture of the case 101, the focal length of the EMR emitted by the delivery optics 106 is fixed, and can be configured such that it does not impact the side of the mask 108, so as to cause injuries to the operator of the fractional ablation system 100. The control module 102 is in communication with the EMR source 104, which in turn is operatively connected to the delivery optics 106.

In one exemplary variant of the present invention, the control module 102 can be in wireless communication with the EMR source 104. In another variant, the control module 102 may be in wired communication with the EMR source 104. In another exemplary variant of the present invention, the control module 102 can be located outside of the case 101. In another variant, the EMR source 104 is located outside of the case 101. In still another variant, the control module 102 and the EMR source 104 are located outside of the case 101. It is also possible that the mask 108 is not connected to the case 101.

The control module 102 provides application specific settings to the EMR source 104. The EMR source 104 receives these settings, and generates EMR based on these settings. The settings can control the wavelength of the EMR, the energy delivered to the skin, the power delivered to the skin, the pulse duration for each EMR pulse, the fluence of the EMR delivered to the skin, the number of EMR pulses, the delay between individual EMR pulses, the beam profile of the EMR, and the size of the area within the mask exposed to EMR. The energy produced by the EMR source 104 can be an optical radiation, which is focused, collimated and/or directed by the delivery optics 106 to the mask 108. The mask 108 can be placed on a target area of a patient's skin, and may provide a damage pattern on the target area of the skin with a fill factor in the range from 0.1% to 90%. The fill factor is the percentage of the target area exposed to the EMR that is emitted by the EMR source 106.

In one exemplary embodiment, the EMR source 106 is one of a laser, a flashlamp, a tungsten lamp, a diode, a diode array, and the like. In another exemplary embodiment, the EMR source 106 is one of a $CO_2$ laser and a Er:YAG laser.

Prior to being used in a dermatological treatment, the system 100 shown in FIG. 1A can be configured by a user. For example, the user may interface with the control module 102 in order to specify the specific settings usable for a particular procedure. The user may specify the wavelength of the EMR, the energy delivered to the skin, the power delivered to the skin, the pulse duration for each EMR pulse, the fluence of the EMR delivered to the skin, the number of EMR pulses, the delay between individual EMR pulses, the beam profile of the EMR, and the size of the area within the mask exposed to EMR. The EMR source 104 may be set to produce a collimated pulsed EMR irradiation with a wavelength ranging from 400 to 11,000 nm, and preferably near 3.0 μm when using an Er:YAG laser and near 10.6 μm when using a $CO_2$ laser as the EMR source. The collimated pulsed EMR irradiation may be applied which has a pulse duration in the range of 1 μs to 10 s, preferably in the range of 100 μs to 100 ms, and more preferrably in the range of 0.1 ms to 10 ms, and fluence in the range from 0.01 to 100 J/cm$^2$, and preferably in the range from 1 to 10 J/cm$^2$. The applied EMR should be able to achieve at least a temperature rise within the exposed areas of the skin that is sufficient to cause thermal damage to the epidermis 110 and/or the dermis 112. The peak temperature sufficient to cause thermal damage in the exposed tissues is time dependant and at least in the range of 45° C. to 100° C. For exposure times in the range of 0.1 ms to 10 ms the minimum temperature rise required to cause thermal damage is in the range of approximately 60° C. to 100° C. The depth of thermal damage can be adjusted by proper choice of wavelength, fluence per pulse and number of pulses.

During the dermatological treatment, the system 100 produces EMR 120 which is directed to the target area of the skin 114, as shown in FIG. 1B. The EMR 120 may be pulsed multiple times to create the appropriate affect and irradiation in the target area of the skin 114.

After the dermatological treatment is completed, the target area of the skin 114 is likely damaged in specific places. The application of the EMR 120 creates a prearranged thermal skin damage 130 in an epidermal tissue 110 and the dermal tissue 112. It should be noted that the thermal skin damage 130 extends through the epidermal tissue 10 and into the dermal tissue 112 only to a predetermined depth. The mask 108 controls in a location where the thermal skin damage 130 is created. The thermal skin damage 130 generally accounts for only 0.1% to 90% of the skin surface area in the target area. A fill factor is defined as the ratio of surface area of the target area of skin thermally damaged by EMR to surface area of the target area of the skin.

In an exemplary embodiment of the present invention, the thermal skin damage 130 may extend through the epidermal tissue 110 and through the entirety of the dermal tissue 112. In another exemplary embodiment of the present invention, the thermal skin damage 130 may occur principally in the dermal tissue 112 and minor skin damage may occur in the epidermal tissue 110. It should be noted that it is possible that the pentration depths of each of the micro areas of the thermal skin damage 130 may be different from one another or same as one another. This may be because pigment removal or dermal removal can be separately regulated by varying the density of the micro-damaged areas for either the deeper or superficial damages, e.g., dermal remodeling and pigment adjustment, respectively.

Figure 2:
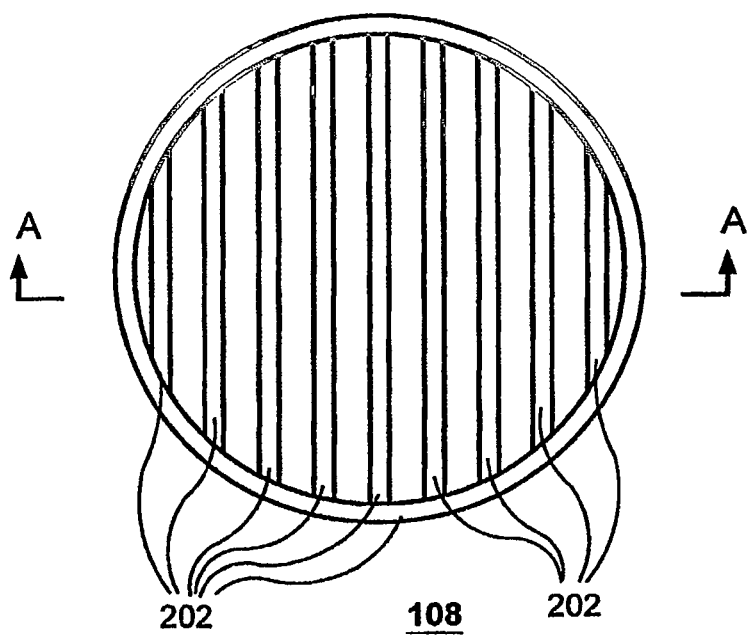
FIG. 2 shows a top view of a first exemplary embodiment of a mask according to the present invention.

FIG. 2 illustrates a top view of a first exemplary embodiment of the mask 108 according to the present invention. The mask 108 includes shielding structured 202. The diameter of the mask 108 should preferably be matched to greater than the size of the diameter of the target area. The target area is defined as the area targeted by the collimated EMR emitted by the EMR source 104, which can be in the range 1-100 mm in diameter, preferably within the range of 5 to 20 mm. This diameter of most of the currently commercially available $CO_2$ and Er:YAG laser systems can match the diameter of the exposed area. The width of shielding structures 202 within the mask 108 should be in the range of 50 to 300 µm. The width of the apertures of the mask 108 that are formed by the shielding structures should be in the range of 10-1000 µm, and preferably in the range of 50 to 300 µm. The shielding-exposure ratio surface area covered by the of shielding structures 202 to the surface area exposed by the apertures effects the clinical efficacy and provides side effects of the dermatological treatment. This also determines the fill factor and the pattern of the thermal damage of the skin. The depth of thermal damage is determined by the number of pulses, the fluence of the EMR and the wavelength of the EMR. The shielding-exposure ratio of the mask 108 will vary for different dermatological treatments, particular patient needs, particular patient indications, skin types and body areas.

The mask 108 may have a large shielding-exposure ratio at the edge of the mask 108 to generate a transition zone at the edge of resurfaced area. This technique is called "feathering." It avoids a sharp macroscopically visible demarcation between treated and untreated areas. In another preferred embodiment, a mask may be used that has a large shielding-exposure ratio at the edge of a conventionally resurfaced area to generate a transition zone.

Figure 3:
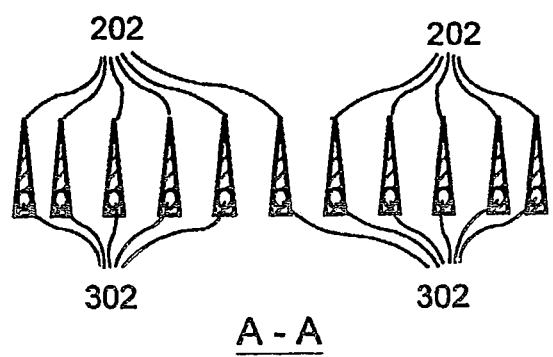
FIG. 3 shows a cross-sectional view of the mask of FIG. 2.

The surface of the mask 108 should preferably have a minimal absorption at the wavelength generated by the EMR source 104 for the particular dermatological process. Such absorption can decrease the undesirable heating of the mask 108. The mask 108 may be coated by a metal material for affectuating a minimal absorption of the EMR. The design of the shielding structures 202 of the mask 108, a cross-section A-A of which is shown in FIG. 3, generally takes into consideration safety aspects, including a back-reflected EMR in order to avoid EMR inflicted accidents. The shielding structures 202 are shaped in a peaked manner to minimize the amount of back reflected EMR. Also, with the mask 108 being connected to the case 101 the distance between the delivery optics 106 and the mask 108 is fixed, thereby minimizing the chances that EMR would be reflected back towards the user by hitting the edge of the mask 108. Additionally, the microstructure of the mask 108 can have a periodicity preferably in the range of the wavelength of the EMR emitted by the delivery optics 106. This configuration can diffuse the collimated EMR emitted by the delivery optics 106 into a highly scattered beam so as to decrease the risk of EMR-related accidents.

In one exemplary embodiment, the metal coating of the mask 108 may be composed of gold, silver, or copper materials, or the like. In another exemplary embodiment, the microstructure of the surface of the mask 108 may have a periodicity in the range of the wavelength of the EMR emitted by the delivery optics 106.

The mask 108 may also have a configuration so as to provide effective skin cooling during the exposure thereof with the EMR radiation. Skin cooling provides significant anesthetic effects, and has other advantages related to the pattern induced by the EMR radiation. The mask 108 can be cooled prior to the beginning of the dermatological procedure, during the procedure by spraying an evaporative agent or a precooled liquid onto the mask 108 between the successive EMR pulses, or during the procedure by introducing a cool or cold liquid into microchannels 302 (shown in FIG. 3) running through the mask 108. The cooling of the mask 108 has a secondary advantage in that such cooling of the mask 108 decreases the rate of the EMR absorption by the mask 108, as the rate of the EMR absorption by the metals increases with the increasing temperature.

In order to provide skin cooling as described above, the temperature of the mask 108 should be in the range of 37° C. to −20° C., and preferably 10° C. to −4° C. The mask 108 can both protect and cool the portions of the skin surface that are not exposed to EMR emitted by the EMR source 104. In addition to cooling and shielding portions of the skin surface, the mask 108 allows the debris ejected during ablative procedures to escape, and thereby not interfere with the beam delivery for successive pulses. For example, the areas that are not exposed to the laser are being cooled by the mask 108, i.e., the areas that are provided between the affected areas. In another exemplary embodiment, all areas (i.e., both the affected and nonaffected areas) are cooled to provide anesthesia, and to reduce over-damaging the superficial levels of the damaged areas.

FIG. 3 illustrates a cross-section A-A of the mask 108 of FIG. 2. The cross-section A-A shows the microchannels 302 that run through at least the shielding structures 202 of the mask 108. A cooling agent, e.g., either a liquid or gas, may circulate through these microchannels 302 during a dermatological procedure, thereby removing heat from the protected skin and the mask 108 itself.

Figure 4:
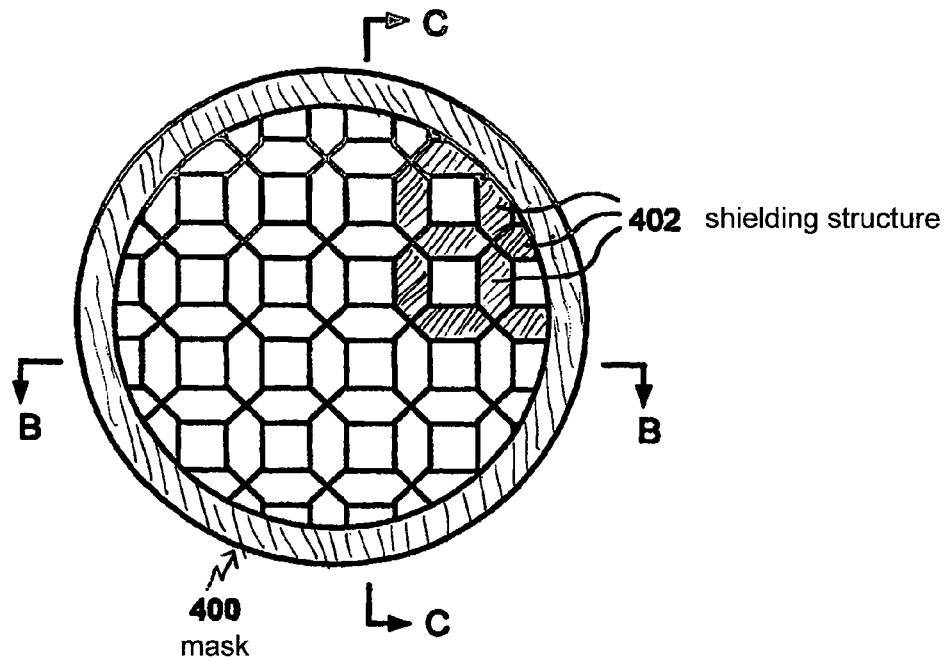
FIG. 4 shows a top view of a second exemplary embodiment of the mask according to the present invention.
Figure 5:
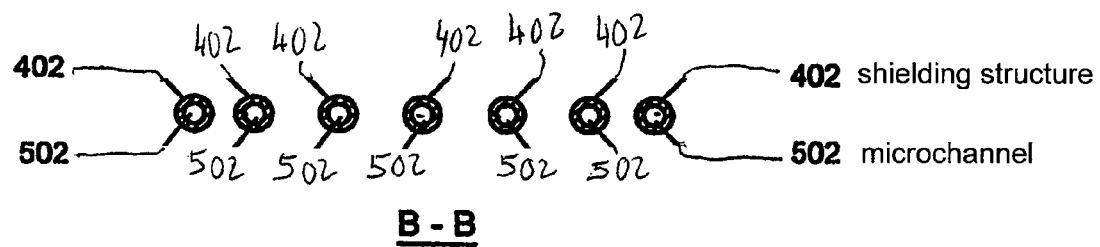
FIG. 5 shows a cross-sectional view of the mask of FIG. 4.
Figure 6:
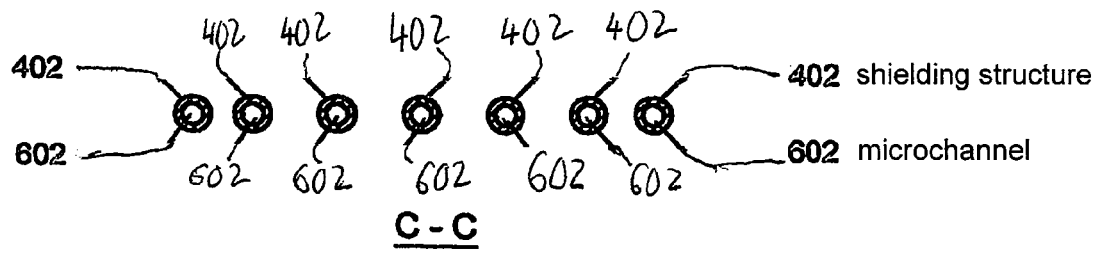
FIG. 6 shows a cross-sectional view of another variant of the mask of FIG. 4.

FIG. 4 illustrates a top view of a second embodiment of the mask 400 according to the present invention. The mask 400 differs from the mask 108 only in the layout and design of the shielding structures 402. The details of the mask 400 are in all other respects substantially similar to those of the mask 108. The shielding structures 402 are cylindrical in shape, as indicated in cut-away cross-sections B-B and C-C, shown in FIGS. 5 and 6, respectively. The shielding structures 402 of the mask 400 contain microchannels 502 and 602, which are capable of carrying a cooled liquid or gas so as to cool the mask 400 and the masked portions of the target area of the skin. The microchannels 502, 602 intersect at the intersection of the shielding structures 402.

In an exemplary embodiment of the present invention, the microstructures 502, 602 are not required to intersect at the intersection of the shielding structures 402.

In an exemplary embodiment of the present invention, the mask 108 is an ablative mask. An ablative mask includes multiple sections having various thicknesses. Prior to a procedure, the ablative mask is attached to the skin with an adhesive. During the procedure having multiple EMR pulses, the ablative mask is ablated, such that the thickness of each of the multiple sections is diminished, potentially gradually exposing different areas of the skin to the EMR pulses. The ablative mask can be composed of various materials including polymer materials. The ablative mask can be easily produced by imprinting a pattern therein.

A particular dermatological treatment, i.e., the removal of tattoos, shall be described in further detail. Tattoo removal may be performed with a combination of an ablative EMR and the mask 108. In particular, utilizing the $CO_2$ laser and/or the Er:YAG laser may be appropriate for this application. During this dermatological procedure, the tattoo can be exposed to ablative EMR radiation with the mask 108 providing a fill factor of the target area in the range of 10 to 90%, and preferably in the range of 25 to 70%. Preferably, the mask 108 is applied under pressure to the skin, which minimizes the blood flow during the procedure. Limiting the blood flow during the procedure allows a deeper ablation of the skin surface before blood can interfere with the EMR radiation, thereby limiting the ablation depth. Multiple pulses of ablative EMR radiation can be applied to the individual areas of the tattoo until the desired ablation depth is reached. The desired ablation depth can be in the range of 100 µm to 5 mm. This exemplary procedure can cause a specific fraction of the tattoo that is controlled by the mask 108 to be immediately ablated. Wound healing may be enhanced because only a fraction of the surface is ablated.

The removal of tattoos utilizing fractional resurfacing may be augmented using a short pulsed EMR, preferentially absorbed by the tattoo particles either before or after the application of the fractional resurfacing. In a short pulsed-laser application, the laser may be pulsed for short periods of time, preferably for less than 1 µs in duration. The EMR source used in this type of procedure can preferably be a Q-switched ruby laser, a Nd:YAG laser, a KTP laser and/or an Alexandrite laser. The objective of this procedure is to release the pigment within areas that are not exposed to fractional resurfacing ablation. The released pigment particles may drain in the ablated channels, and can be flushed from the area after the procedure by the blood resident in the target area and/or an external rinsing agent, e.g., saline. Several such procedures may be utilized until the desired clearance of the tattoo has occurred.

Figure 7A:
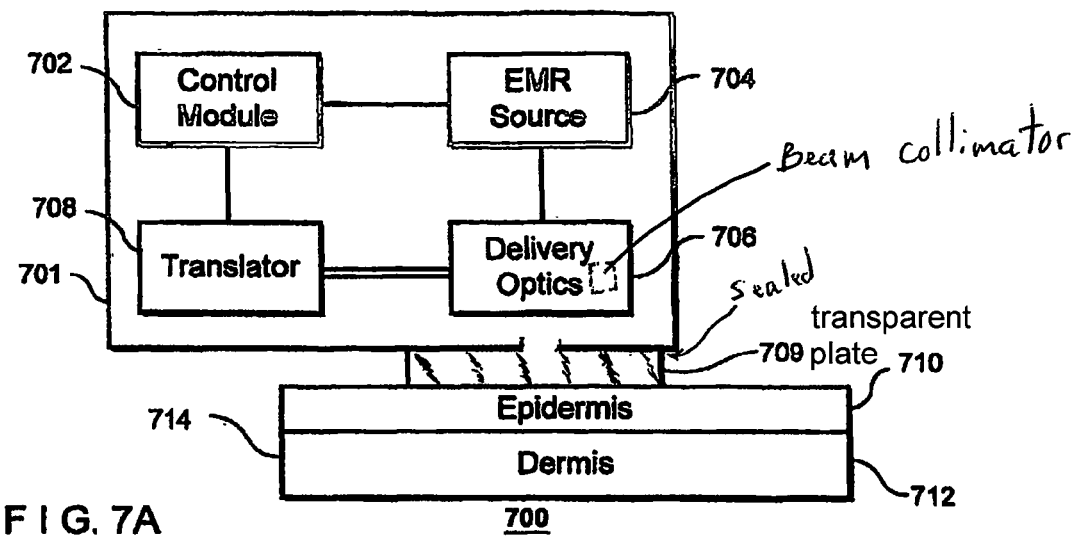
FIGS. 7A and 7B show progressive illustrations of a second exemplary embodiment of the fractional resurfacing system for conducting various dermatological treatments at various stages of use according to the present invention.
Figure 7B:
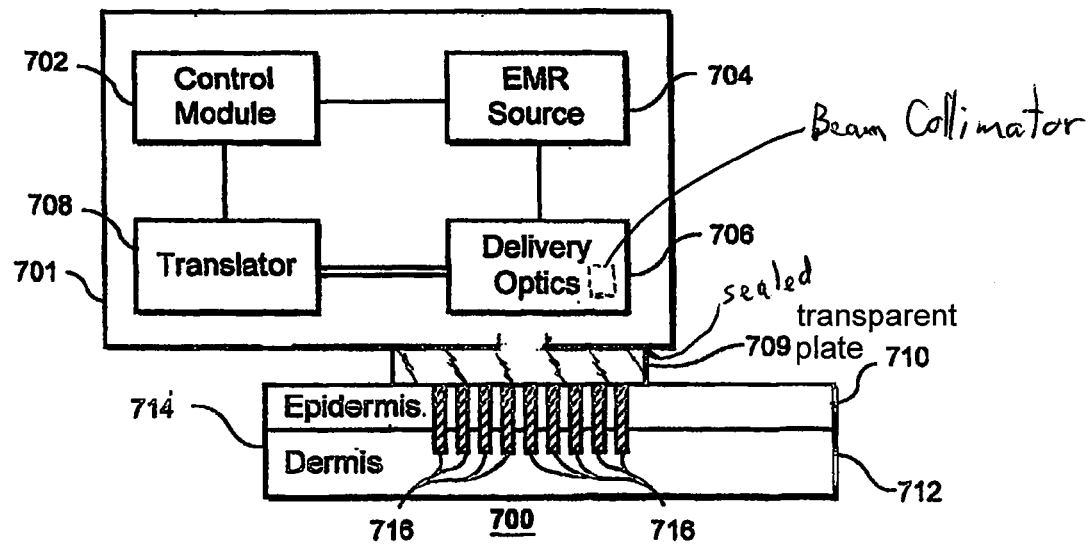

As an alternative to the fractional resurfacing using a mask, a second embodiment of a fractional resurfacing system 700, as shown as the progressive use thereof in FIGS. 7A-7B, can be used. The system 700 can include a case 701, a control module 702, an electromagnetic radiation ("EMR") source 704, delivery optics 706, an x-y translator 708 and an optically transparent plate 709. The case 701 may contain the control module 702, the EMR source 704, the delivery optics 706 and the translator 708. As with the system 100, an aperture may be formed through a sidewall of the case 701. The optically transparent plate 709 may be placed in registration with the aperture that is formed through the sidewall of the case 701. Placing the plate 709 in registration with the aperture formed through the sidewall of the case 701 seals the system 700, which contains sophisticated translation mechanisms, e.g., the delivery optics 706 and the translator 708. The control module 702 is in communication with the translator 708 and the EMR source 704, and the EMR source 704 is operatively connected to the delivery optics 706.

In one exemplary variant of the present invention, the control module 702 can be located outside of the case 701. In another exemplary variant, the EMR source 704 is located outside of the case 701. In still another variant, the control module 702 and the EMR source 704 are located outside of the case 701.

The control module 702 provides application specific settings to the EMR source 704, and controls the x-y translator 708. The EMR source 704 receives these settings, and generates EMR based on these settings. The settings can control the wavelength of the energy produced, the intensity of the energy produced, the fluence of the energy produced, the duration of the dermatological procedure, the pulse length of each of the EMR pulses administered during the procedure, the spatial distance between individual exposure areas 716 (shown in FIG. 8), the shape of individual exposure areas 716, the pattern defined by individual exposure areas 716, and the fill factor of the target area. It should be noted that the thermal skin damage caused to individual exposure areas 716 extends through the epidermal tissue 710 and into the dermal tissue 712 only to a predetermined depth. The EMR source 704 can be a laser or other light source. The EMR produced by the EMR source 704 can be delivered through a fiber, waveguide or mirrors if the source is located outside the delivery optics 706. Alternatively, if the EMR source 704 is located in a close vicinity to the skin 714, the EMR source 704 produces the EMR directly to the delivery optics 706. The energy produced by the EMR source 704 may be focused and/or directed by focusing optics in the delivery optics 706 to one of the an individual exposure areas 716, shown in FIG. 8. Each of the individual exposure areas 716 are located within the target area of the skin 714, and are relatively small compared to the target area of the skin 714. The target area of the skin 714 can generally be 1 $cm^2$ in size and each of the individual exposure areas 716 may be 100 µm in diameter.

In an exemplary embodiment of the present invention, the optics of the delivery optics 706 may contain a beam collimator or focusing optics. In another exemplary embodiment of the present invention, the thermal skin damage caused to individual exposure areas 716 may extend through the epidermal tissue 710 and through the entirety of the dermal tissue 712. In another exemplary embodiment of the present invention, the thermal skin damage caused to individual exposure areas 716 may principally occur in the dermal tissue 712 and only minor thermal damage may occur in the epidermal tissue 710. It should be noted that it is possible that the pentration depths of each of the micro areas of the thermal skin damage caused to individual exposure areas 716 may be different from one another or same as one another. This may be because pigment removal or dermal removal can be separately regulated by varying the density of the micro-damaged areas for either the deeper or superficial damages, e.g., dermal remodeling and pigment adjustment, respectively. In a further exemplary embodiment of the present invention, the predetermined depth of the thermal skin damage caused to individual exposure areas 716 is approximately 300 μm.

Prior to use in a dermatological treatment and similarly to the use of system 100, the system 700, as shown in FIG. 7A, can be configured by a user. In particular, the user interfaces with the control module 702 in order to specify the specific settings to be used for a particular procedure. The user may specify the desired damage pattern, the wavelength of the energy produced by the EMR source 704, the intensity of the energy produced, the fluence of the energy produced, the length of time the treatment will take and the pulse duration of the EMR source 704. During the treatment, the translator 708 moves the delivery optics 706 across sequential portions of the target area of the skin 714 in order to treat the entire target area. The target area is treated when the system 700 delivers EMR to individual exposure areas 716 of the target area. The individual exposure areas 716 may be targeted serially and/or in parallel. When one of the portions of the target area has been completely treated, the system 700 is moved to the next portion of the target area. For example, the system 700 is moved at the completion of irradiation of each portion of the target area until the desired skin surface damage pattern is achieved for the entire area. The system 700 can be moved using discrete movements from one sequential portion to the next, i.e., stamping mode, or using continuous movement across the skin surface, i.e., continuous scanning mode. In either case, the movement of the delivery optics 706, driven by the translator 708, is controlled by the control unit 702 and likely matched with the movement of the system 700 by the operator (or the user) in order to provide the desired surface damage pattern to the target area of the skin 714.

In an exemplary embodiment of the present invention, the system 700, while operating in the continuous scanning mode, can deliver EMR to a particular individual exposure area 716, then, after exposure of such area 716, translate along the skin of the target area, and thereafter deliver a further EMR to another individual exposure area 716 separated from the previous particular individual exposure area 716 by non-irradiated region. In another exemplary embodiment of the present invention, the system 700, while operating in the continuous scanning mode, can deliver EMR to a particular group of individual exposure areas 716, for example the top row of individual exposure areas 716 (shown in FIG. 8), then, after exposure of such areas 716, translate along the skin of the target area, and deliver a further EMR to another group of individual exposure areas 716, for example the second row of individual exposure areas 716 (shown in FIG. 8), separated from the particular group of individual exposure areas 716 by non-irradiated areas.

In an exemplary embodiment of the present invention, the system 700 includes a position sensor, which is in communication with the control module 702. The position sensor is capable of sensing the relative velocity as between the skin 114 and the case 701. The position sensor can be an optical mouse, wheels, track ball, conventional mouse, and the like.

In another exemplary embodiment of the present invention, the system 700 targets individual exposure areas 716 one at a time. Administering EMR to the individual exposure areas 716 one at a time decreases the amount of pain experienced by the subject. A time period of 50 milliseconds may be provided between each administration of EMR to each of the individual exposure areas 716. Thereby controlling the amount of pain experienced by the subject and avoiding bulk heating of the tissue targeted by the system 700. In still another exemplary embodiment of the present invention, the system 700 targets a predetermined number of individual exposure areas 716 at a time. Limiting the number of predetermined target areas 716 targeted at one time limits the amount of pain experienced by a patient. Targeting a large number of individual exposure areas 716 at one time requires targeting a collectively large area of skin, which excites many nerve endings simultaneously, therefore causing the subject a proportionally large amount of pain. Targeting fewer individual exposure areas 716 causes a subject less pain, but causes a procedure to take longer.

In a further exemplary embodiment of the present invention, the system 700 creates individual exposure areas 716 having a separation distance between each of the individual exposure areas 716 of approximately at least 125 μm and at most 500 μm, preferably, the separation distance is approximately at least 250 μm.

Before the initiation of a dermatological procedure, the optically transparent plate 709 can be brought in a direct contact with the skin surface covering the target area. The optically transparent plate 709 can be composed out of any material having good thermal conductivity, and being transparent over a broad range of the visible and near infrared spectrum. The plate 709 seals the system 700, which contains sophisticated translation mechanisms, and provides cooling to the target area of the skin 714. The plate 709 can provide cooling to the target area of the skin 714 in two ways: heat conduction and heat convection. Heat conduction transfers heat through the optically transparent plate 709 to the case 701, which provides cooling by circulating a coolant agent through the case 701 of the system 700. The entire optically transparent place 709 can also be cooled prior to application to the target area of the skin 714. Alternatively, heat convection can be utilized for this procedure. An evaporating agent sprayed onto the optical window or onto a compartment in good thermal contact with the window may also be utilized. The delivery of the evaporating agent can be administered during the procedure between EMR pulses through a valve, which can be controlled by a thermostat with a temperature sensor at the optical plate.

In one embodiment, of the present invention the optically transparent plate 709 can be composed of sapphire or quartz. In another embodiment of the present invention, the system 700 can be moved multiple times over the same portion of the skin 714 until the desired fill factor is achieved. In yet another embodiment, multiple procedures can be performed to achieve the desired effect.

During the dermatological procedure, the EMR source 704 emits EMR having a wavelength in the range of 400-12,000 nm. Preferably the EMR has a wavelength in one of the following ranges: 1,300 to 1,600 nm, 1,850 to 2,100 nm, 2,300 to 3,100 nm and around 10,640 nm. Depending on the application, a single wavelength or a combination of different wavelengths may be utilized. The EMR source 704 can be a diode laser, a fiber laser, a solid state laser, a gas laser, and the like. The pulse duration can range from 100 μs to 100 ms, and preferably in the range from 500 μs to 15 ms, and more preferably in the range from 1.5 ms to 5 ms. The energy density per pulse within an individual exposure area 716 may be in the range of 0.1 to 100 $J/cm^2$, preferably 1 to 32 $J/cm^2$, and more preferably 1.5 to 3 $J/cm^2$. The energy per pulse within an individual exposure area 716 may be in the range of 1 mJ and 10 mJ, and preferably 5 mJ.

In an exemplary embodiment of the present invention, the EMR source 704 is a 1.5 μm laser system, preferably a Reliant FSR prototype, manufactured by Reliant Technologies, Palo Alto, Calif., is used.

After the dermatological treatment is completed, the target area of the skin 714 is damaged in a specific pattern. The application of EMR creates the thermal skin damage in an epidermis 710 and a dermis 712 of the skin 714. The radiation provided by the EMR source 704 is delivered to the skin 714 within multiple small individual exposure areas 716, shown in FIG. 7B, through the delivery optics 706. The delivery optics 706 can deliver multiple individual beams across the target area of the skin surface.

Figure 8:
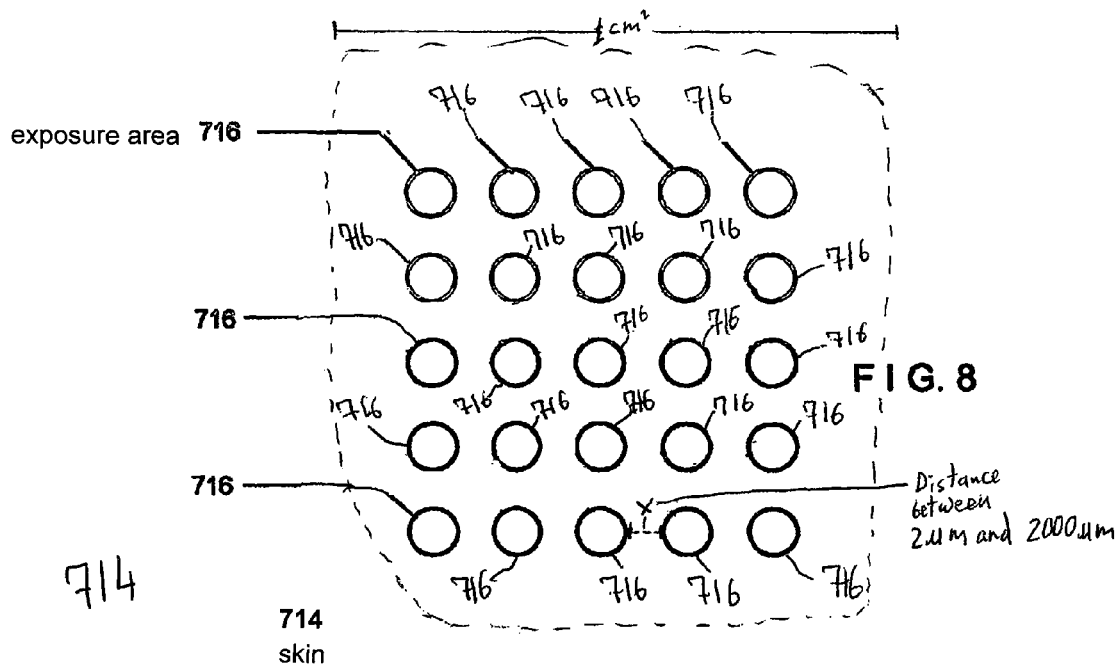
FIG. 8 shows a top view of small individual exposure areas created by the fractional resurfacing system of FIGS. 7A and 7B.

FIG. 8 illustrates a top view of the small individual exposure areas 716 of the epidermis. The shape of the individual exposure areas 716 may be circular (shown in FIG. 8), elliptical, rectangular, linear or irregular with a lateral diameter of the smallest dimension in the range of 1-500 µm. The fill factor of the target area can be approximately 20-40%.

The system 700 can create multiple individual exposure areas 716 through heating, ablation, removal, photothermal coagulation, thermal necrosis and/or stimulation. The multiple areas can be exposed sequentially or simultaneously. Sequential exposure may be achieved by scanning or moving an energy source which may be either pulsed, shuttered or continuous. Simultaneous exposure can be achieved, for example, by an array of sources or a multi-array of lenses. The array of sources may be a uni-dimensional array, a bi-dimensional array or the like. The array can be moved relative to the skin, and one or multiple passes of treatment can be performed in a target area.

Figure 9:
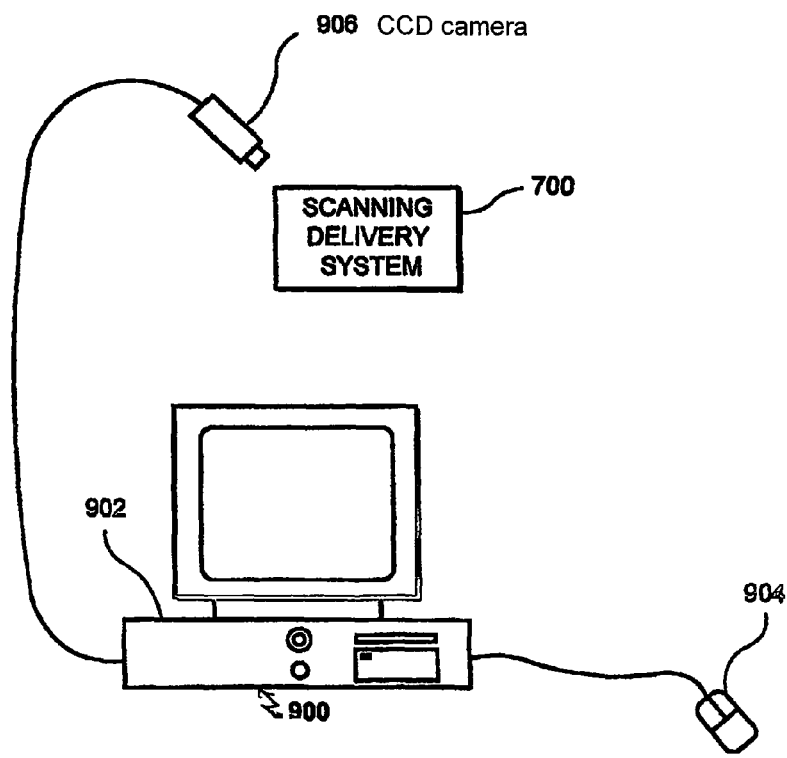
FIG. 9 shows an exemplary embodiment of a system for monitoring the location of the fractional resurfacing system of FIGS. 7A and 7B.

FIG. 9 illustrates an exemplary embodiment of a monitoring system 900 according to the present invention. The monitoring system 900 tracks the movement of the system 700, and feeds such positional information to the control module 702. The control module 702 utilizes this information to appropriately instruct the translator 708 to position the delivery optics 706, such that the appropriate damage pattern is achieved across the target area of the skin 714. The monitoring system 900 may use a computer 902, a mouse 904, and a charge coupled device ("CCD") camera 906. In particular, the computer 902 receives the positional information about the system 700 from the CCD camera 906. The computer then updates the control module 702 based on this positional information as to the current position of the system 700. The control module 702 utilizes this information to cause the system 700 to create the appropriate damage pattern on the skin 714 within the target area. In addition, the monitoring system can utilize additional motion detecting devices, including, wheels or any other motion sensor.

The shape of the individual exposure areas 716 and the relative pattern represented by all of the individual exposure areas 716 may vary. The individual exposure areas 716 can have a circular, elliptical, rectangular, linear or irregular shape. The average distance between individual regions of exposed skin surface may be in the range between 10 to 2000 µm, and preferably in the range of 100 to 500 µm. The macroscopic pattern of the individual exposure areas 716 may be a field of uniformly distributed individual exposure areas 716 with constant spacing throughout the target area, randomly distributed individual exposure areas 716 within the target area, and/or regularly distributed individual exposure areas 716 with constant average spacing with randomly shifted location. In particular, having regularly distributed individual exposure areas 716 with constant average spacing with randomly shifted location may be useful to minimize undesirable effects, which may occur during multiple treatments. Such multiple treatments are utilized to cover the entire area as homogeneously as possible by the individual exposure areas 716 during the course of multiple treatments. However, uniformly distributed individual exposure areas 716 with constant spacing throughout the target area may create unwanted spatial distributions similar to moire patterns, resulting in spatial interference macroscopic patterns generated with a distance in between the areas of exposure which have a significant spatial period. In order to minimize the occurrence of moire patterns, a randomized shift within the range of 10 to 50% of the average distance between individual exposure areas 716 during a single scan may be utilized.

The treatment can be performed in by a single treatment covering the skin surface with a specific surface damage pattern, or by multiple treatments either performed at the same visit or during different treatment visits. Individual or multiple exposures can be used to achieve the appropriate thermal damage in particular individual exposure areas 716.

Fractional resurfacing may cause portions of the epidermis to be thermally damaged or ablated, thereby reducing the efficacy of the barrier function of the epidermis and in particular decreasing the stratum corneum. This facilitates the delivery of drugs or specific substances to the dermis and epidermis which can either enhance the effects of the treatment, or decrease the side effects caused by partial damage of the epidermis and/or dermis. Groups of drugs and substances, which may enhance the efficacy of skin remodeling include growth factors, collagen byproducts, collagen precursors, hyaluronic acid, vitamins, antioxidants, amino acids and supplemental minerals among others. Groups of drugs and substances, which may decrease side effects, can be steroidal anti-inflammatory drugs, non-steroidal anti-inflammatory drugs, antioxidants, antibiotics, antiviral drugs, antiyeast drugs and antifungal drugs.

In an exemplary embodiment of the present invention, the vitamins that are used may be vitamin C and/or vitamin E. The supplemental minerals used are copper and zinc. The antioxidants can be vitamin C and/or vitamin E.

In a clinical observation, enhanced wound healing was observed for fractional resurfacing as compared to conventional resurfacing. The forearm skin of a white, male Caucasian was exposed to pulsed $CO_2$ laser radiation with identical settings of the illuminating laser beam with a beam diameter of approximately 3 mm, a Coherent Ultra Pulse Laser, CPG handpiece, at approximately 300 mJ/pulse. One area was exposed to the laser beam without benefit of a mask while another area was partially shielded by a cooled mask. More pronounced erythema was evident at the conventionally resurfaced test site as compared to the fractionally resurfaced test site.

The fill factor of the target area may be monitored by sensing the electrical impedance of the skin from a location on the skin within the target area to a remote location on the skin outside of the target area during or after treatment. An indicator capable of staining the defects in the stratum corneum (for example, trypan glue) or transdermal waterloss are effective indicators of the fill factor of the target area.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

What is claimed is:

1. A method for treating dermatological conditions, comprising:
   controlling an electromagnetic radiation source to generate an electromagnetic radiation;
   causing the electromagnetic radiation to be applied to a target area of skin; and
   preventing at least one portion of the target area of the skin from being exposed to the electromagnetic radiation;

wherein the radiation is configured to at least one of thermally damage or ablate epidermal tissue and dermal tissue of the target area of the skin extending from a surface of the skin through an entire depth of the epidermal tissue and to at least a particular depth within the dermal tissue of the skin, and wherein a width of the at least one portion of the target area is at least 50 μm and at most 300 μm.

2. The method of claim 1, wherein the preventing step is performed using a masking arrangement.

3. The method of claim 1, wherein at least 0.1% of the target area is prevented from being exposed to the electromagnetic radiation.

4. The method of claim 1, wherein at most 90% of the target area is prevented from being exposed to the electromagnetic radiation.

5. The method of claim 2, wherein a dimension of a portion of the masking arrangement is at least 50 μm and at most 300 μm.

6. The method of claim 2, wherein the masking arrangement is configured to define at least one aperture.

7. The method of claim 6, wherein a dimension of the at least one aperture is at least 10 μm and at most 1000 μm.

8. The method of claim 6, wherein a dimension of the at least one aperture is at least 50 μm and at most 300 μm.

9. The method of claim 2, wherein the masking arrangement is cooled.

10. The method of claim 1, wherein the electromagnetic radiation source is an ablative laser.

11. The method of claim 1, wherein the electromagnetic radiation source is at least one of a carbon dioxide laser and an Er:YAG laser.

12. The method of claim 1, further comprising:
controlling a further electromagnetic radiation source to generate a further electromagnetic radiation; and
applying the further electromagnetic radiation to the target area of the skin.

13. The method of claim 12, wherein the further electromagnetic radiation source is one of a Q-switched ruby laser, a Nd:YAG laser, a KTP laser and an Alexandrite laser.

14. The method of claim 1, further comprising introducing a substance to the target area, wherein the substance comprises at least one of a growth factors, a collagen byproduct, a collagen precursor, hyaluronic acid, a vitamin, an antioxidant, an amino acid and a supplemental mineral.

15. The method of claim 1, wherein the step of causing the electromagnetic radiation to be applied to a target area of skin comprises providing the electromagnetic radiation to a plurality of exposure areas on the skin surface, and wherein a smallest dimension of the exposure areas along the skin surface area is between about 1 μm and about 500 μm.

16. The method of claim 1, wherein the percentage of the target area that is exposed to the electromagnetic radiation is between 20% and 40%.

* * * * *